United States Patent
Pfeffer

(10) Patent No.: US 6,620,078 B2
(45) Date of Patent: *Sep. 16, 2003

(54) FITNESS TRIAGE SYSTEM AND NUTRITION GETS PERSONAL

(75) Inventor: Linda Pfeffer, Los Angeles, CA (US)

(73) Assignee: Aerobics and Fitness Association of America, Sherman Oaks, CA (US)

(*) Notice: Subject to any disclaimer, the term of this patent is extended or adjusted under 35 U.S.C. 154(b) by 140 days.

This patent is subject to a terminal disclaimer.

(21) Appl. No.: 09/734,284

(22) Filed: Dec. 11, 2000

(65) Prior Publication Data

US 2002/0082144 A1 Jun. 27, 2002

(51) Int. Cl.$^7$ ................................................ A63B 71/00
(52) U.S. Cl. ................................ 482/9; 482/8; 128/920; 434/236
(58) Field of Search ............................... 482/1–9, 900, 482/901; 128/920, 923; 434/236–238

(56) References Cited

U.S. PATENT DOCUMENTS

| | | | |
|---|---|---|---|
| 4,464,122 A | * | 8/1984 | Fuller et al. ................. 434/262 |
| 5,673,691 A | * | 10/1997 | Abrams et al. ............... 434/238 |
| 5,890,128 A | * | 3/1999 | Diaz et al. ..................... 705/2 |
| 6,283,761 B1 | * | 9/2001 | Joao ............................ 434/236 |

* cited by examiner

Primary Examiner—Glenn E. Richman

(74) Attorney, Agent, or Firm—Patrick F. Bright; Bright & Lorig

(57) ABSTRACT

Fitness Triage® is a system and method for prioritizing delivery of personalized exercise and injury prevention information based on identification and analysis of user-specific health and fitness indicators. By providing answers to questions concerning key health risk factors, conditions, and habits, exercise information is delivered to the user based on the level of potential risk and other considerations associated with his/her participation in an fitness program. Based on the Fitness Triage® analysis of user data, the delivery of information is identified and prioritized according to one of three levels of potential risk. The user is thus informed of the level of risk associated with his/her participation in exercise, and the recommended precautions based on his/her individual health profile. The Fitness Triage® system is accessed by the user directly through the Internet or licensed Intranet, or through the guidance of an intake coordinator, personal trainer, or other qualified health/fitness professional.

Working in tandem with Fitness Triage®, Nutrition Gets Personal® relies upon Fitness Triage®'s screening indicators of health and exercise risk before posing its own questions of nutritionally-specific risk factors. Nutrition Gets personal® provides meal plans based on a consumer's nutritional goals, exercise habits and goals, following its own nutritionally-specific screening questions identifying health and nutritional risks which serve to modify the meal plans themselves. Information concerning nutritional risks is similarly delivered to the consumer, along with access to topical resources on the Web and general tips towards healthy eating.

9 Claims, 3 Drawing Sheets

FITNESS TRIAGE

FITNESS TRIAGE SYSTEM AND NUTRITION GETS PERSONAL

BACKGROUND OF THE INVENTION

The invention relates to the field of nutrition science and individualized identification and enhancement of potential nutritional benefits and the prevention of adverse nutritional contra-indications and physical injuries as related to diet according to individual habits and health risk indicators.

On May 30–31st, 2000 the new dietary guidelines (5th edition) for Americans was issued by the Department of Health and Human Services and the Department of Agriculture at the National Nutrition Summit. According to DHHS Secretary Donna Shalala, Ph.D. she noted that these new guidelines "offer most practical value and scientific information than ever before to help American consumers make the smartest possible decisions when it comes to what we eat."[1] Those guidelines offer information to help select the right kinds of foods and in proper amounts. However, it is up to the consumer to make the appropriate choices, without any benefit of performing health risk assessments beforehand.

There are Web sites galore that appeal to those who wish to lose weight, however, none offer health risk assessments. That is, there is no follow-up information targeting their health risks prior to engaging a new meal program. Moreover, not all diet plans are designed by a registered dietician. For those that are, not all make accommodations for allergy-specific consumers or for those with varied dietary restrictions.[2] For those whose goals are other than weight loss, there also remains a dearth of resources to reach consumers with athletic performance needs, muscle building requirements, general health or pregnancy status. Since a key component to healthy eating includes exercise and health risk assessment beforehand, there isn't a comprehensive nutritional program that includes all these elements into one integrated program, except for Fitness Triage® and Nutrition Gets Personal®.

[1]"New Dietary Guidelines", L. Bren, FDA Consumer, Sept.–Oct. 2000, p.10
[2]"A Guide to Rating the Weight-Loss Websites", Tufts University, A Special Supplement to the Health and Nutrition Newsletter, 2000, p.2

SUMMARY OF THE INVENTION

The Fitness Triage® and Fitness Gets Personal® fill this void by providing consumers and professionals a reliable system, program and method of access that provides individualized identification, evaluation and prioritized delivery of exercise information and precautions according to an established database of researched information. Nutrition Gets Personal® offers meal plans based on a consumer's nutritional goals, exercise habits and goals, following screening questions identifying health and nutritional risks which serve to modify the meal plans themselves. Information concerning nutritional risk is similarly delivered to the consumer, along with access to topical resources on the Web and general tips towards healthy eating.

The invention enables the user/consumer to access reliable information regarding his/her actual/planned exercise and nutritional experience, thus enhancing the potential for both safe and effective physical activity and nutritional adherence.

The invention enables the user to access this information directly or through a qualified health/fitness professional who directs the data entry. Methods of access include direct access through the Internet for a small fee associated with membership or subscription; access through an intake coordinator via phase for a small fee; and access directed by a qualified professional at a non-determined fee. The invention also provides the user with the opportunity to re-evaluate the user's initial results based on health, behavioral or nutritional status changes.

BRIEF DESCRIPTION OF THE DRAWINGS

FIG. 1

1.A User accesses the Fitness Triage® system through the Internet at the website of the Aerobics & Fitness Association of America, www.afaa.com. See U.S. Pat. No. 6,159,131, issued Dec. 12, 2000, entitled *Fitness Triage System and Method* and co-pending, concurrently filed U.S. patent application Ser. No. 09/734,413 entitled *Fitness Triage System and Exercise Gets Personal.* The entirety of that patent and that patent application are incorporated herein by reference. All users are provided with a login number (username). Each user then creates his/her own password. The individual who accesses the Fitness Triage® system may do so for his/her own information, or acting on behalf of another. A personal trainer or physician are examples of professionals who may utilize the service on behalf of another. As a user initiates the login process, the program will first recognize whether or not the user has a valid login number (username). If the login number is valid, and this is a first login for the user, the program will request that the user create a personal password. Return users with a valid login number will enter both their username and password to complete the login process. Invalid login numbers are rejected.

Figure 1:
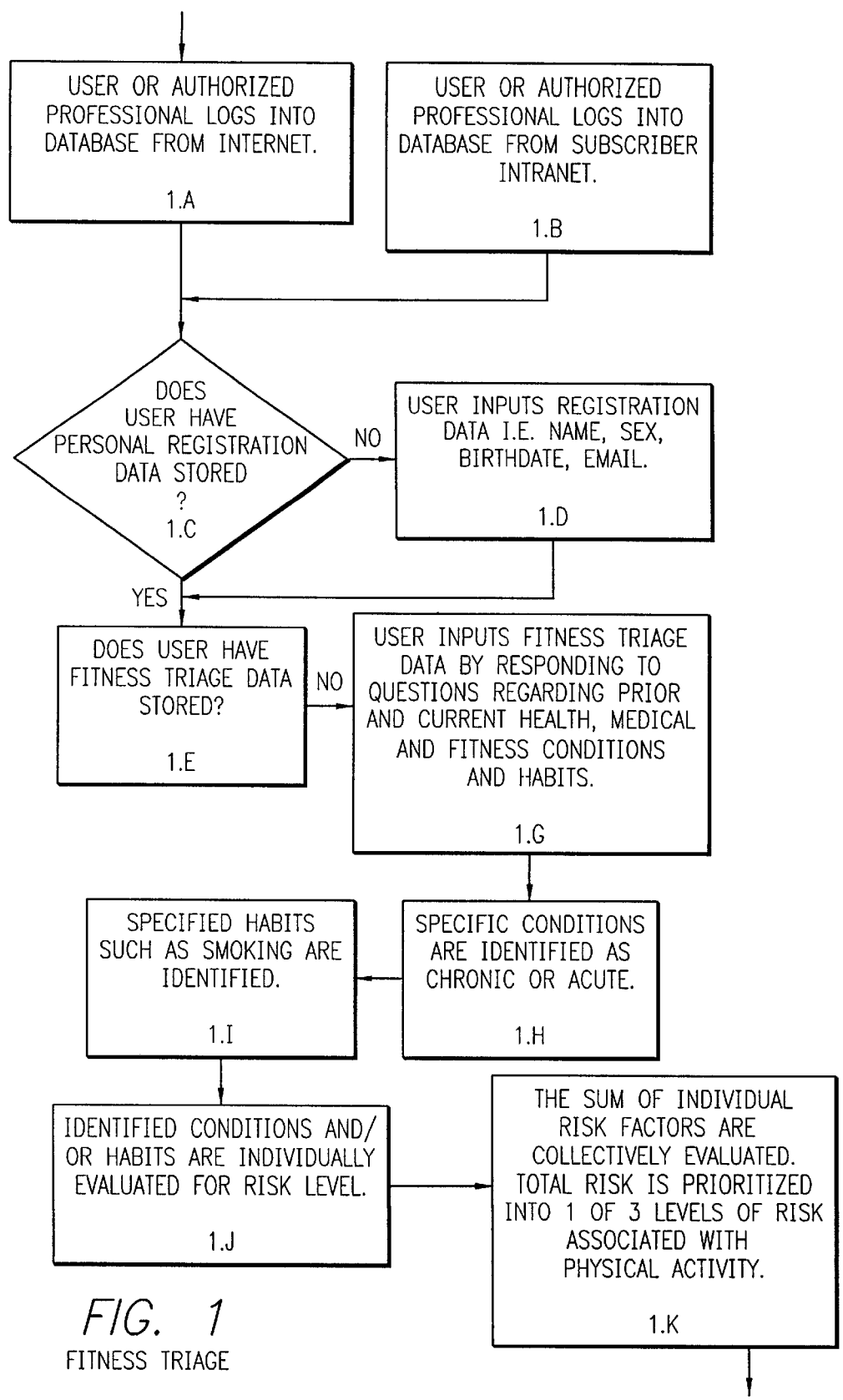
FIG. 1 describes the data input and analysis stages of the Fitness Triage® system process.
Figure 2:
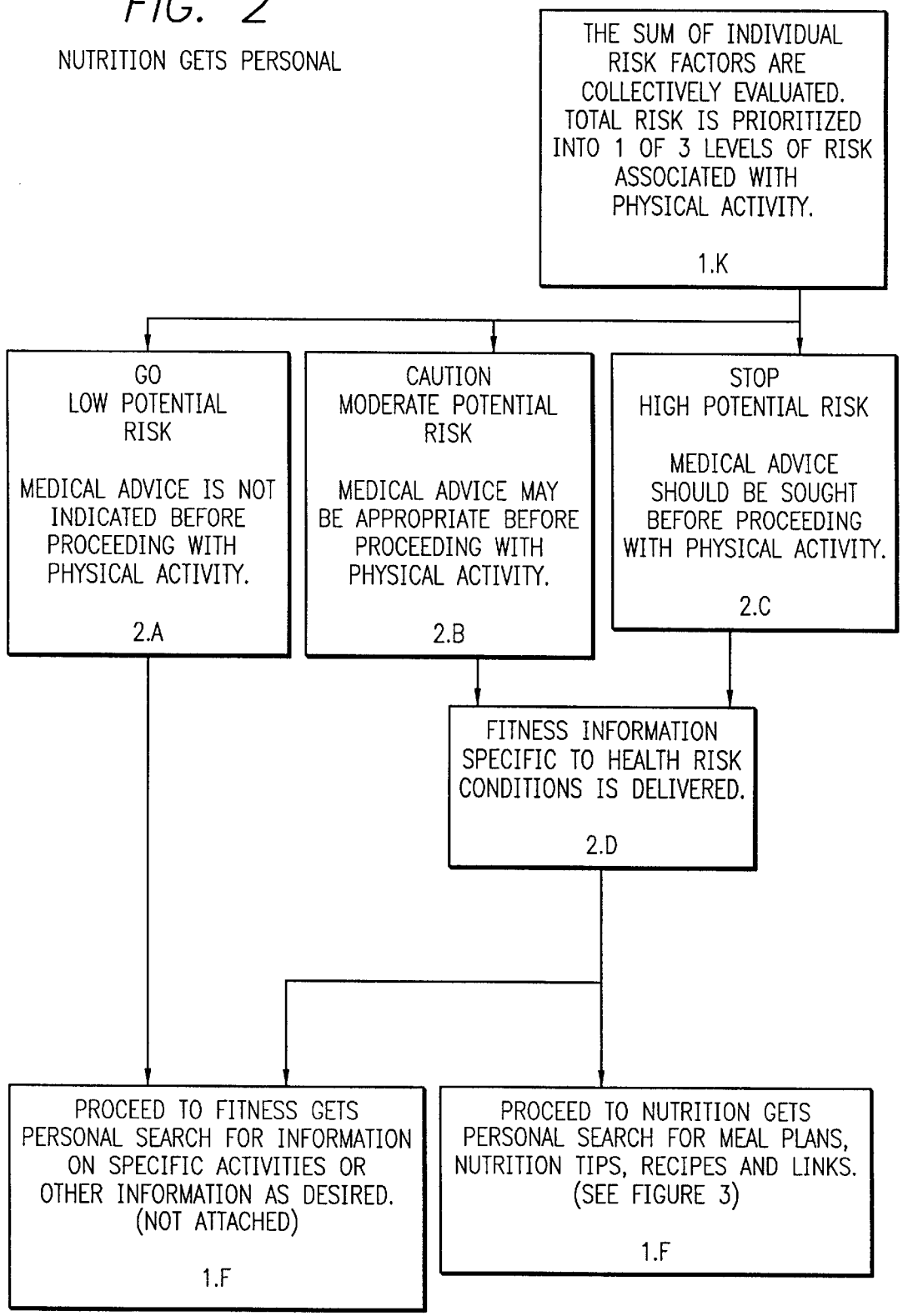
FIG. 2 describes prioritization of potential risk and the delivery of information.

1.B User accesses the Fitness triage® system through a corporate Intranet. AFAA sells corporate subscription packages which allow corporations to provide employees or health/fitness professionals with access to the Fitness Triage® system through either the Internet or through the corporate Intranet. All other aspects of access are the same as described for FIG. 1.A.

1.C Upon completing login, the program will recognize whether or not the user has personal registration data stored. Personal registration data for each user is stored in a database on the AFAA server.

1.D If the program does not find any stored registration information, the user will be requested to complete a brief registration form. Completion of all fields is required. The fields include; first and last name, birth date, gender, and email address.

1.E After valid registration is acknowledged, the program will recognize whether or not the user has Fitness Triage® data stored. Personal health data obtained through the Fitness Triage® system is stored for each user in a database on the AFAA server.

Figure 3:
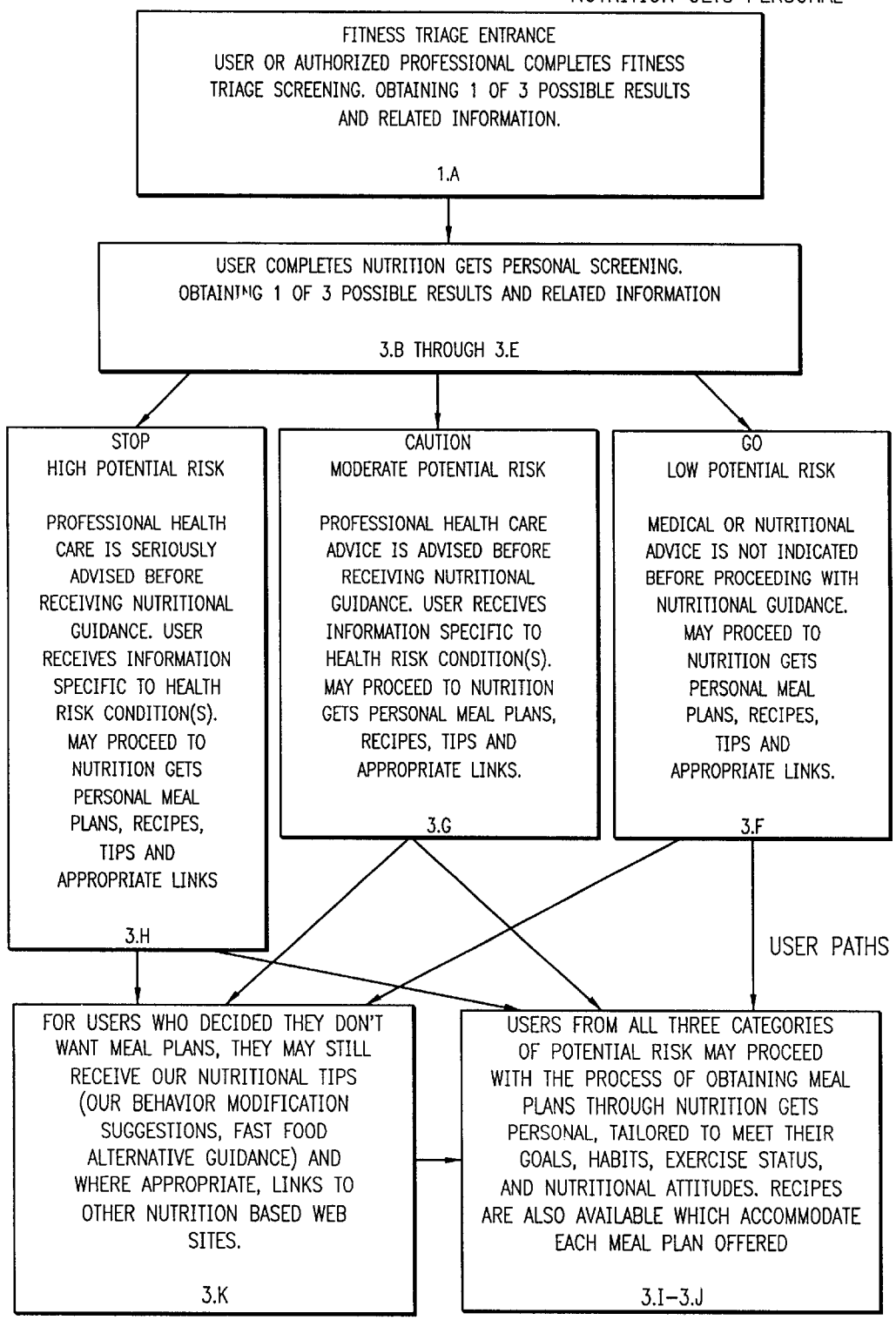
FIG. 3 describes the final process of the user's search for and delivery of discretionary information.

1.F If the user has previously completed the Fitness Triage® he/she may proceed directly to the Nutrition Gets Personal® screening questions (see FIG. 3) or to Fitness Gets Personal® database for consultation.

1.G If the program does not find any stored health information, the user will be requested to complete a brief health questionnaire. The questionnaire is divided into 7 sections. In the first 4 sections the user simply selects items that apply from the lists provided. The first section requests information about current condition or habits that relate to overall risk. The second section gathers information related to medical care or clearance. The third section gathers information about any current health concerns. The fourth section gathers health history and chronic disease/condition information. In section five the user is asked to list current medications. In section six the user lists other medical conditions, if any, that were not included in the list provided. Finally, the user is asked the date of his/her last medical exam. The user then submits the form. This is a secure transmission using SSL technology.

1.H The program scans the medical conditions such as illness or injury submitted and identifies those items which are chronic, acute, and/or symptomatic. The program scans the habits and other health-related conditions submitted and identifies any that may pose a risk, i.e., smoking or pregnancy.

1.J All conditions and habits are individually evaluated for level of potential risk. Each is assigned a numerical weighted value. For example, an affirmative response to the query "Recent Surgery/Wound" is weighted more heavily than an affirmative response to "Tobacco Use".

1.K The sum of all individual weighted values is evaluated collectively, analyzing the total risk of all conditions in conjunction with other another. In other words, the individual effect of one condition may create a moderate risk potential. However, that condition accompanied by one or more other conditions, may create a high risk potential. Likewise, an affirmative response to the query, "Are you cleared by a physician to exercise?" may reduce the level of overall risk. This portion of the Fitness Triage® process analyzes all possible combinations and prioritizes the information that will be delivered to the user according to 1 to 3 levels of potential risk associated with physical activity. The user is delivered a message that indicates the level of risk according to his personal indicators.

FIG. 2

2.A. The first level of risk that is identified in the Fitness Triage® system is that of low potential risk. Medical advice is not indicated before proceeding with physical activity. This is graphically indicated to the user by use of a green "GO" button, similar to a green traffic light, and the instructions that they are cleared to proceed with searching for additional information.

2.B The second level of risk that is identified in the Fitness Triage® system is that of moderate potential risk. The user is advised that they have one or more conditions that may indicate a health problem. The user is strongly advised to seek professional health care advice and a physician's clearance before attempting any physical activity. This is graphically indicated to the user by use of a yellow "CAUTION" button, similar to a yellow traffic light.

2.C The third level of risk that is identified in the Fitness Triage® system is that of high potential risk. This is graphically indicated to the user by use of a red "STOP" button, similar to a red traffic light. The user is advised that they have one or more conditions that may indicate a health problem. They are strongly advised to seek professional health care advice and a physician's clearance before attempting any physical activity.

2.D Users receiving results as either the "Caution" or "Stop" level of potential risk will also be delivered information specific to the conditions they have indicated. For example, a user indicating diabetes will receive information regarding diabetes and exercise. The user is additionally advised that the information pages are not intended, and should not be used, as a substitute for proper medical advice and/or exercise prescription.

2.E Users receiving results from either of the three categories of potential risk may proceed with the process of seeking information from the Fitness Gets Personal@ database (where they may receive information on specific activities such as aqua aerobics or running, or on weight management or strength training, just to name a few of the possible topics) or gain information from Nutrition Gets Personal@ where they will be further screened for nutrition-specific health risks before receiving meal plans and tips based on their goals, health/fitness conditions, nutritional behaviours and attitudes.

FIG. 3

3.A The Nutrition Gets Personal® database is composed of 3 primary content sources: 1) a set of screening questions upon which a meal is based; 2) a links page for further Web resource information; and 3) a general tips area for behavioral modification suggestions towards healthier eating.

3.B If the program does not find any stored nutritional screening information, the user will be requested to complete a brief nutritional questionnaire regarding behavioral habits, specific health conditions, nutritional goals, exercise habits, and nutritional attitudes. The questionnaire is divided into 5 sections. The first section requests generalized participant information, including activity level, age, height, weight, and gender. The second section asks a series of health conditions and behaviors which impact any dietary plan, including cholesterol, blood pressure, and fastening glucose measurements, along with such factors as family history of heart disease/cancer/diabetes, current conditions such as allergies, pregnancy and recent hospitalization, and such behaviors as smoking and alcohol imbibing. The third section gathers information about the user's nutritional goals. The fourth section collects data on the user's exercise habits. The fifth section seeks to discover a user's attitude and behavioral habits concerning nutrition in general. The user then submits the form. This is a secure transmission using SSL technology.

3.C The program flags health conditions that are present, and identifies them as acute, chronic, benign, and/or symptomatic.

3.D The program scans the exercise, eating and behavioral habits, attitudes, goals and other health-related conditions submitted and identifies if any pose a risk or require dietary adjustment, e.g. smoking or pregnancy.

3.E Depending on what data is given by the user, a comparison to standardized health measures of risk are made and evaluated for level of potential risk. Each is assigned a categorical and weighted evaluation based on each health condition/behavior/habit answer given. That is, an answer can result in a categorical assessment of "low risk", meaning that the candidate may proceed to obtain meal plan advice. In a separate instance, the presence of a food allergy which calls for dietary adjustment would pose "moderate to high risk" which in combination with another moderate risk (e.g. taking medication for hypothyroidism) would result in a "high risk" potential.

3.F The first level of risk identified in the Nutrition Gets Personal® system is that of low potential risk. Here, neither medical nor nutritional advice is indicated before proceeding with nutritional guidance. This is indicated to the user by allowing him to proceed and obtain the meal plans prepared by the system, along with a graphic notation of a green "GO" button, much like a traffic signal.

3.G The second level of risk identified in the Nutrition Gets Personal® system is that of moderate potential risk. The user is advised that he has one or more conditions that may indicate a health or nutrition problem. The user is strongly advised to seek professional health care advice and a physician's clearance before proceeding in obtaining dietary advice through this system. This is graphically depicted to the user by a yellow "Caution" button, much like an amber traffic light.

3.H The third level of risk identified in the Nutrition Gets Personal® system is of high potential risk. This is graphically indicated to the user by the use of a red "STOP" button, similar to a red traffic light. The user is advised that he has one or more conditions that may indicate a health or nutritional problem. The user is strongly advised to seek professional health care advice and a physician and/or dietician's clearance before proceeding to obtain meal plans through the Nutrition Gets Personal® system.

3.I Users receiving results of "Caution" or "Step" level of potential risk will also be given information specific to the conditions they have indicated. For example, a user indicating diabetes will receive information regarding diabetes and nutrition. Moreover, links into the Fitness Gets personal system are also provided, tapping into a large cache of fitness content. The user is additionally advised that the information pages are not intended, nor should not be used, as a substitute for proper medical advice and/or nutritional prescription.

3.J Users receiving result from either of the three categories of potential risk may proceed with the process of obtaining meal plans through Nutrition Gets Personal@, along with accessing its resource links and general nutritional tips. Meal plans are tailored for each user, including substitution items and recipes. This information includes behavioral modification suggestions for those seeking to lose weight, best alternatives for fast food dining, and links to reputable Web site sources for nutrition-related information.

3.K For users who decide that they would rather no gain meal plans, they are then provided with the behavioral modification suggestions, fast food alternative guidance, and links to other nutrition-based Web sites for more nutrition information.

What is claimed is:

1. A data processing apparatus for delivering user-specific nutrition program comprising:
   a central controller including a CPU and a memory operatively connected to said CPU;
   at least one terminal that transmits to said central controller, user-specific information comprising said user's health, medical, fitness and nutrition conditions;
   said memory and said central controller comprising a program, to be executed by said CPU, for separately and collectively evaluating the risks associated with said user-specific information to determine whether said user may begin a nutrition program;
   wherein said central controller receives said user-specific information from said terminal and outputs a statement as to whether said user may begin a nutrition program, and whether said user should obtain medical clearance before beginning such a program.

2. The apparatus of claim 1 wherein said memory and said central controller and said program enable a user who may begin a nutrition program to access nutrition information suitable for said user based information related to nutrition and health questions and appropriate answers, meal plans, nutrition tips and where appropriate, links to relevant nutrition-based Web sites.

3. A method of determining whether a user can begin a nutrition program, and, where the user may begin such a program, for determining an appropriate nutrition program for said user, using a central controller comprising a CPU, a memory operatively connected to said CPU and a program to be executed by said CPU for determining whether said user may proceed with such a nutrition program, and, where appropriate to proceed, for determining said appropriate nutrition program for said user, the method comprising the steps of:
   inputting said user-specific information about said user's heath, medical, fitness and nutrition conditions;
   individually evaluating each of said health, medical, fitness, and nutrition conditions for risk level;
   collectively evaluating the individual risks levels to determine whether said user may proceed with a nutrition program, and, where appropriate to proceed, outputting a suitable nutrition program for said user.

4. A data processing apparatus for determining whether a user may proceed with a nutrition program, and, where appropriate to proceed, for determining an appropriate nutrition program for said user comprising:
   a CPU and a memory operatively connected to said CPU, said memory comprising a program for execution by said CPU, said CPU and memory cooperating to receive user-specific inputs concerning said user's health, medical, fitness and nutrition conditions, and to determine, from said user-specific inputs, the risks associated with each of said inputs, and the collective risk to said user from the risks associated with each of said inputs to determine whether said user may proceed with a nutrition program, or whether said user should seek medical advice before beginning such a nutrition program.

5. A method of determining whether a user may begin a nutrition program, or whether said user should first obtain medical advice before beginning such a program, using a central controller comprising a CPU and a memory operatively connected to said CPU, and comprising a program for execution by said CPU for determining steps, the method comprising the steps of:
   inputting user-specific health, medical, fitness and nutrition conditions;
   individually evaluating the risks associated with each of said conditions;
   collectively evaluating the resulting individuals risks;
   determining whether said user may begin a nutrition program, and, where said user may begin, with what limitations or restrictions, or determining whether said user should obtain medical clearance before beginning a nutrition program; and
   devising a nutrition program appropriate for said user by having the CPU execute said program and output a user-appropriate nutrition program.

6. The method of claim 5 further comprising opening to said user access to databases including information appropriate for a nutrition program for said user.

7. A method for determining whether a user may begin a nutrition program comprising the steps of:
   receiving user-specific inputs concerning said user's health, medical, fitness and nutrition conditions relative to an appropriate nutrition program for said user;

evaluating the risk associated with each of said conditions, and evaluating these individual risks collectively; and outputting information as to whether said user may proceed with a nutrition program or should first obtain medical clearance before proceeding with a nutrition program.

8. The method of claim 7 further comprising the step of outputting an appropriate nutrition program for said user, if appropriate.

9. A data processing apparatus for determining whether a user can undertake a nutrition program for said user comprising:

a terminal adapted to communicate with a central controller that determines and evaluates, collectively, the individual risks associated with each user-specific input about said user's health, medical, fitness and nutritional conditions, and outputs the resulting risk information;

said terminal being adapted to transmit to said central controller said risk information and further adapted to receive from the central controller a decision as to whether said user may proceed with a nutrition program or whether said user should first obtain medical advice before beginning a nutrition program.

* * * * *